United States Patent [19]
Kingsman et al.

[11] Patent Number: 4,615,974
[45] Date of Patent: Oct. 7, 1986

[54] YEAST EXPRESSION VECTORS

[75] Inventors: Alan J. Kingsman; Susan M. Kingsman, both of Islip, England

[73] Assignee: Celltech Limited, Berkshire, England

[21] Appl. No.: 408,826

[22] Filed: Aug. 17, 1982

[30] Foreign Application Priority Data

Aug. 25, 1981 [GB] United Kingdom ............... 8125934
Mar. 23, 1982 [GB] United Kingdom ............... 8208422
Jun. 16, 1982 [GB] United Kingdom ............... 8217496

[51] Int. Cl.$^4$ .................... C12P 2/1; C12P 21/02; C12N 15/00; C12N 1/18
[52] U.S. Cl. ..................... 435/68; 435/70; 435/172.3; 435/317; 435/256; 935/6; 935/28; 935/69
[58] Field of Search ............... 435/68, 70, 172.3, 317, 435/255, 256; 935/6, 28, 69

[56] References Cited

U.S. PATENT DOCUMENTS 4,387,162 6/1983 Aigle et al. ..................... 435/172

FOREIGN PATENT DOCUMENTS 0011562 5/1980 European Pat. Off. .
0057350 8/1982 European Pat. Off. .
2068969 8/1981 United Kingdom .

OTHER PUBLICATIONS

Clarke, et al: PNAS 77 No. 4 (1980) pp. 2173-2177.
Beggs, et al: Nature 283 (Feb. 1980), pp. 835-840.
Tuite, et al, The EMBO J. 1 No. 5 (1982), pp. 603-608
Valenzuela et al: Nature 298 No. 5872 (Jul. 1982), pp. 347-349.
Hitzeman et al: Nature 293 (Oct. 1981), pp. 717-721.
Hitzeman et al., The Journal of Biol. Chem., vol. 255, pp. 12073-12080, Dec. 25, 1980.
Clarke et al., Nature, vol. 287, pp. 504-509, Oct. 9, 1980.
Broach et al., Cell, vol. 21, pp. 501-508, Sep. 1980.
Hatsley et al., Nature, vol. 286, pp. 860-864, Aug. 28, 1980.
Broach et al., Gene 8, pp. 121-133 (1979).
Tschumper et al., Gene, vol. 10, pp. 157-166 (1980).
Ammerer et al., Recombinant DNA, Proceedings of the Third Cleveland Symposium on Macromolecules, pp. 185-197 (Jun. 22-26, 1981).

Primary Examiner—Alvin E. Tanenholtz
Attorney, Agent, or Firm—Cushman, Darby & Cushman

[57] ABSTRACT

There are described a number of plasmid vectors suitable for the expression of genetic material, at various levels in yeasts. The plasmids each comprise a yeast selective marker, a yeast replication origin and a yeast promoter positioned relative to a unique restriction site in such a way that expression may be obtained of a polypeptide coding sequence inserted at the restriction site. The promoters used are derived from the 5' region of a gene coding for a yeast glycolytic enzyme e.g. phosphoglycerate kinase (PGK), or from the 5' region of the yeast TRP1 gene. In one Example a plasmid contains a promoter derived from both the 3' and 5' regions of the PGK gene. The replication systems used involve the yeast $2\mu$ replication origin or an autonomous replicating sequence (ARS) stabilized with an ARS stabilizing sequence (ASS). The replication systems allow for a choice of high or low copy number per cell. The promoter sequences allow for a choice of high or low expression level. A kit including vectors having a combination of these alternative features is described. Yeast expression vectors including a gene for coding for human interferon-α are described.

11 Claims, 19 Drawing Figures

TRP I FRAGMENT (1·45 Kb)
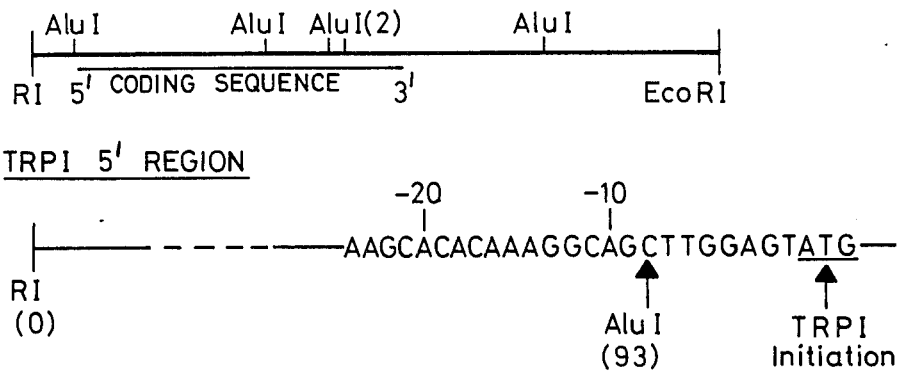
TRP I 5' REGION
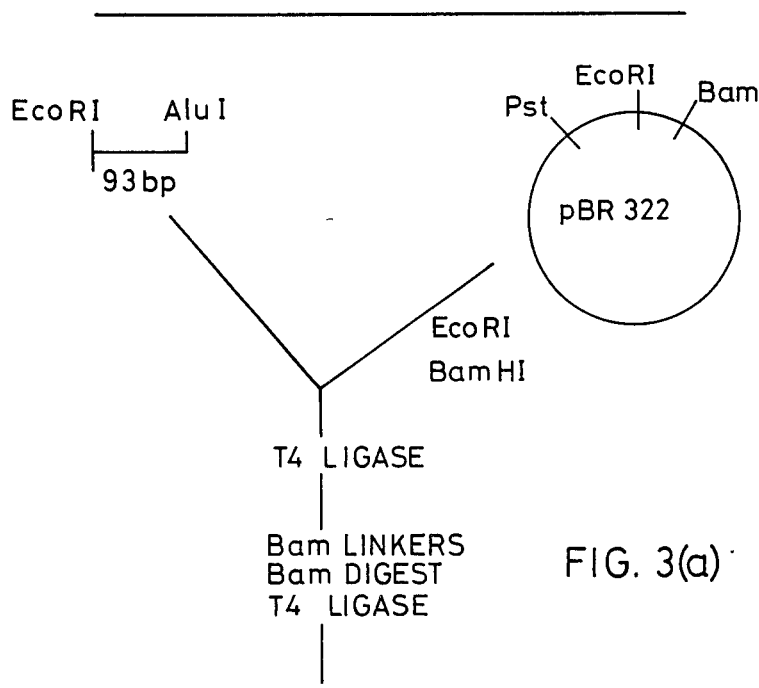
FIG. 3(a)

CATACTATAT ATATAATATA GAAGCATTTA ATAGAACAGC ATCGTAATAT ATGTGTAGTT

60

TGCAGTTATG ACGCCAGATG GCAGTAGTGG AAGATATTCT TTTATTGAAA AATAGCTGTC

120

ACCTTACGTA CAATCTGATC CGGAGCTTTT CTTTTTTTGC CGATTAAGAA TTCGGTCGAA
EcoRI

180

AAAAGAAAAG GAGAGGGCCA AGAGGGAGGG CATTGGTGAC TATTGAGCAC GTGAGTATAC

240

GTGATTAAGC ACACAAAGGC AGCTTGGAGT ATG

FIG. 6.

a)
```
    270          280
    |            |
    MEKAKAKGVEVVLPVDFIIA
                     ⊢S⊣
    290          300
    |            |
    DAFSASANTKTVTDKEGIPA
                     ⊢Pv
    310          320
    |            |
    GWQGLDTGTESEKLFAATVA
    ⊣
    330          340
    |            |
    KATVILWNGPPGVFEFEKFA
                     ⊢RI⊣
    350          360
    |            |
    AGTKALLDEVVKSTAAGNSV
    370          380
    |            |
    IIGGGDTATVAKKYGVTDKI
                       ⊢Bg
    390          400
    |            |
    SHVSTGGGASL
    ⊣
``` b)

FIG. 12

-226
*
AGCCTGCTCT CACACATCTT TCTTCTAACC AAGGGGTGTT TAGTTTAGTA

-176
*
GAACCTCGTG AAACTTACAT TTACATATAT ATAAACTTGC ATAAATTGGT

-126
*
CAATGCAAGA AATACATATT TGTCTTTTCT AATTCGTAGT TTTTCAAGTT

-76
*
CTTAGATGCT TTCTTTTTCT CTTTTTTACA GATCATCAAG AAGTAATTAT

-26                  -1 +1
*                    .
CTACTTTTTA CAACAAATAT AAAACA ATG TCT TTA TCT TCA AAG TTG
                            MET SER LEU SER SER LYS LEU

```
-226
*
AGCCTGCTCT CACACATCTT TCTTCTAACC AAGGGGTGTT TAGTTTAGTA

-176
*
GAACCTCGTG AAACTTACAT TTACATATAT ATAAACTTGC ATAAATTGGT

-126
*
CAATGCAAGA AATACATATT TGTCTTTTCT AATTCGTAGT TTTTCAAGTT
```

FIG.13.

```
-76                    278
*
CTTAGATGCT TTCTTTTTCT CTTTTTTACA GATCATCAAG AAGTAATTAT

-26         301              283
*
CTACTTTTTA CAACAAATAT AAAACA ATG TCT TTA TCT TCA AAG TTG TCT
                             MET SER LEU SER SER LYS LEU SER
                              1    .    .    .    5    .    .

24          230           257          219
*
GTC CAA GAT TTG GAC TTG AAG GAC AAG CGT GTC TTC ATC AGA GTT GAC TTC
VAL GLN ASP LEU ASP LEU LYS ASP LYS ARG VAL PHE ILE ARG VAL ASP PHE
 .   .  10   .   .   .   .   .   .   .   .   .  20   .   .   .   .

75                          279 213
*
AAC GTC CCA TTG GAC GGT AAG AAG ATC ACT TCT AAC CAA AGA ATT GTT GCT
ASN VAL PRO LEU ASP GLY LYS LYS ILE THR SER ASN GLN ARG ILE VAL ALA
 .   .   .   .  30   .   .   .   .   .   .   .   .   .  40   .   .

126      203
*
GCT TTG CCA ACC ATC AAG TAC GTT TTG GAA CAC CAC CCA AGA TAC GTT GTC
ALA LEU PRO THR ILE LYS TYR VAL LEU GLU HIS HIS PRO ARG TYR VAL VAL
 .   .   .   .   .   .  50   .   .   .   .   .   .   .   .   .   .

177
*              Acc I
TTG GCT TCT CAC TTG GGT AGA CCA AAC GGT GAA AGA AAC GAA AAA TAC TCT
LEU ALA SER HIS LEU GLY ARG PRO ASN GLY GLU ARG ASN GLU LYS TYR SER
 .  60   .   .   .   .   .   .   .   .  70   .   .   .   .   .   .

228      220
*
TTG GCT CCA GTT GCT AAG GAA TTG CAA TCA TTG TTG GGT AAG GAT GTC ACC
LEU ALA PRO VAL ALA LYS GLU LEU GLN SER LEU LEU GLY LYS ASP VAL THR
 .   .   .  80   .   .   .   .   .   .   .   .   .  90   .   .

279                             271
*
TTC TTG AAC GAC TGT GTC GGT CCA GAA GTT GAA GCC GCT GTC AAG GCT TCT
PHE LEU ASN ASP CYS VAL GLY PRO GLU VAL GLU ALA ALA VAL LYS ALA SER
 .   .   .   .   .   . 100   .   .   .   .   .   .   .   .   .

330
*
GCC CCA GGT TCC GTT ATT TTG TTG GAA AAC TTG CGT TAC CAC ATC GAA GAA
ALA PRO GLY SER VAL ILE LEU LEU GLU ASN LEU ARG TYR HIS ILE GLU GLU
110  .   .   .   .   .   .   .   . 120   .   .   .   .   .   .

381
*
GAA GGT TCC AGA AAG GTC GAT GGT CAA AAG GTC AAG GCT TCC AAG GAA GAT
GLU GLY SER ARG LYS VAL ASP GLY GLN LYS VAL LYS ALA SER LYS GLU ASP
 .   .   . 130   .   .   .   .   .   .   .   . 140   .   .   .

432  265
*
GTT CAA AAG TTC AGA CAC GAA TTG AGC TCT TTG GCT GAT GTT TAC ATC AAC
VAL GLN LYS PHE ARG HIS GLU LEU SER SER LEU ALA ASP VAL TYR ILE ASN
 .   .   .   .   . 150   .   .   .   .   .   .   .   .   . 160

483                                    246
*
GAT GCC TTC GGT ACC GCT CAC AGA GCT CAC TCT TCT ATG GTC GGT TTC GAC
ASP ALA PHE GLY THR ALA HIS ARG ALA HIS SER SER MET VAL GLY PHE ASP
 .   .   .   .   .   .   . 170   .   .   .   .   .   .   .

534
*
TTG CCA CAA CGT GCT GCC GGT TTC TTG TTG GAA AAG GAA TTG AAG TAC TTC
LEU PRO GLN ARG ALA ALA GLY PHE LEU LEU GLU LYS GLU LEU LYS TYR PHE
 .   . 180   .   .   .   .   .   .   .   .   . 190   .   .   .

585                                                     228
*
GGT AAG GCT TTG GAG AAC CCA ACC AGA CCA TTC TTG GCC
GLY LYS ALA LEU GLU ASN PRO THR ARG PRO PHE LEU ALA
 .   .   .   .   .   . 200   .   .   .   .   .   .
```

1
\* EcoRI
GAATTC GAA AAG TTC GCT GCT GGT ACT AAG GCT TTG TTA GAC GAA GTT GTC
       GLU LYS PHE ALA ALA GLY THR LYS ALA LEU LEU ASP GLU VAL VAL

52
\*
AAG AGC TCT GCT GCT GGT AAC ACC GTC ATC ATT GGT GGT GGT GAC ACT GCC
LYS SER SER ALA ALA GLY ASN THR VAL ILE ILE GLY GLY GLY ASP THR ALA

103                                    Bgl II
\*
ACT GTC GCT AAG AAG TAC GGT GTC ACT GAC AAG ATC TAC CAT GTC TCT ACT
THR VAL ALA LYS LYS TYR GLY VAL THR ASP LYS ILE TYR HIS VAL SER THR

154
\*
GGT GGT GGT GCT TCT TTG GAA TTA TTG GAA GGT AAG GAA TTG CCA GGT GTT
GLY GLY GLY ALA SER LEU GLU LEU LEU GLU GLY LYS GLU LEU PRO GLY VAL

205
\*
GCT TTC TTA TCC GAA AAG AAA TAA AT TGAATTGAAT TGAAATCGAT
ALA PHE LEU SER GLU LYS LYS \*\*\*
                             STOP

251
\*
AGACGAATTT TTTTCTTTTC TCTTTCCCCA TCCTTTACGC TAAAATAATA

301
\*
GTTTATTTTA TTTTTTGAAT ATTTTTTATT TATATACGTA TATATAGACT

351                                                         FIG. 14
\*
ATTATTTATC TTTAATGAT

```
 ↓BamHI
GGATCC ATG GGC TGC AAG TCA AGC TGC TCT GTG GGC TGT GAT CTG CCT CAA
       MET GLY CYS LYS SER SER CYS SER VAL GLY CYS ASP LEU PRO GLN

52
*
ACC CAC AGC CTG GGT AGC AGG AGG ACC TTG ATG CTC CTG GCA CAG ATG AGG
THR HIS SER LEU GLY SER ARG ARG THR LEU MET LEU LEU ALA GLN MET ARG

103
*
AAA ATC TCT CTT TTC TCC TGC TTG AAG GAC AGA CAT GAC TTT GGA TTT CCC
LYS ILE SER LEU PHE SER CYS LEU LYS ASP ARG HIS ASP PHE GLY PHE PRO

154
*
CAG GAG GAG TTT GGC AAC CAG TTC CAA AAG GCT GAA ACC ATC CCT GTC CTC
GLN GLU GLU PHE GLY ASN GLN PHE GLN LYS ALA GLU THR ILE PRO VAL LEU

205
*
CAT GAG ATG ATC CAG CAG ATC TTC AAT CTC TTC AGC ACA AAG GAC TCA TCT
HIS GLU MET ILE GLN GLN ILE PHE ASN LEU PHE SER THR LYS ASP SER SER

256
*
GCT GCT TGG GAT GAG ACC CTC CTA GAC AAA TTC TAC ACT GAA CTC TAC CAG
ALA ALA TRP ASP GLU THR LEU LEU ASP LYS PHE TYR THR GLU LEU TYR GLN

307
*
CAG CTG AAT GAC CTG GAA GCC TGT GTG ATA CAG GGG GTG GGG GTG ACA GAG
GLN LEU ASN ASP LEU GLU ALA CYS VAL ILE GLN GLY VAL GLY VAL THR GLU

358
*
ACT CCC CTG ATG AAG GAG GAC TCC ATT CTG GCT GTG AGG AAA TAC TTC CAA
THR PRO LEU MET LYS GLU ASP SER ILE LEU ALA VAL ARG LYS TYR PHE GLN

409
*
AGA ATC ACT CTC TAT CTG AAA GAG AAG AAA TAC AGC CCT TGT GCC TGG GAG
ARG ILE THR LEU TYR LEU LYS GLU LYS LYS TYR SER PRO CYS ALA TRP GLU

460
*
GTT GTC AGA GCA GAA ATC ATG AGA TCT TTT TCT TTG TCA ACA AAC TTG CAA
VAL VAL ARG ALA GLU ILE MET ARG SER PHE SER LEU SER THR ASN LEU GLN

511
*
GAA AGT TTA AGA AGT AAG GAA TGA AAACT GGTTCAACAT GGAAATGATT
GLU SER LEU ARG SER LYS GLU ***

560
*
TTCATTAATT CGTATGCCAG CTCACCTTTT TATGATCTGC CATTTCAAAG

610
*
ACTCATGTTT CTGCTATGAC CATGACACGA TTTAAATCTT TTTCAAATGT

660
*
TTTTAGGAGT ATTAATCAAC ATTGTATTCA GCTCTTAAGG CACTAGTCCC

710
*
TTACAGAGGA CCATGCTGAC TGATCCATTA TCTATTTAAA TATTTTTAAA

760
*
ATATTATTTA TTTAACTATT TATAAACAA CTTATTTTTG TTCATATTAC

810
*
GTCATGTGCA CCTTTGCACA GTGGTTAATG TAATAAAATA TGTTCTTTGT

860
*
ATTTGGTAAA AAAAAAAAA AAAAAAAAA AAAAAAAAA AAAAAAAA

910
*
AAAAAAAAA AAAAAAAAA AAAACCGGAT CC
                          BamHI
```

FIG. 16.

YEAST EXPRESSION VECTORS

This invention relates to the field of molecular biology and in particular to plasmid vectors suitable for the expression, at various levels, of genetic material in yeasts.

Recently plasmids have been developed that can be used as replication vectors in yeast (Struhl et al (1979) PNAS 76 1035 and Kingsman et al (1979) Gene 7 141).

Yeast replication vectors are capable of autonomous replication within a yeast host organism and are therefore suitable for introducing foreign DNA into yeasts.

The vectors have also been used to isolate a portion of yeast DNA for further analysis. Whilst such known systems are capable of reliable replication within a yeast host organism they are not, to a significant extent, themselves capable of expression of inserted DNA.

The production of useful and interesting polypeptides by the exploitation of recombinant DNA techniques has hitherto been centred around E. coli as a host/vector system (Martial et al (1979) Science 205 602 and Nagata et al (1980) Nature 284 316). In general these expression systems have depended on a plasmid vector containing an E. coli promoter sequence, a ribosome binding site (Shine-Delgarno sequence) and often the first few codons of an E. coli coding sequence to which the "foreign" coding sequence is joined (Hallewell and Emtage (1980) Gene 9 27). In many cases, therefore, fusion proteins are synthesised, although more recently procedures have been developed to allow synthesis of "foreign" proteins without attached E. coli amino acid sequences (Guarente et al (1980) Cell 20 543).

In some situations E. coli may prove to be unsuitable as a host/vector system. For example E. coli contains a number of toxic pyrogenic factors that must be eliminated from any potentially useful pharmaceutical product. The efficiency with which purification can be achieved will, of course, vary with the product. Also the proteolytic activities in E. coli may seriously limit yields of some useful products (e.g. Itakura et al (1977) Science 198 1056). These and other considerations have led to increased interest in alternative host/vector systems, in particular the use of eukaryotic systems for the production of eukaryotic products is appealing. Amongst the eukaryotic organisms suitable for exploitation perhaps the easiest to manage is the yeast *Saccharomyces cerevisiae*. Yeast is cheap, easy to grow in large quantities and it has a highly developed genetic system.

It is an object of this invention to provide a yeast vector system capable of expressing an inserted polypeptide coding sequence.

According to the present invention we provide a yeast expression vector comprising a yeast selective marker, a yeast replication origin and a yeast promoter positioned relative to a unique restriction site in such a way that expression may be obtained of a polypeptide coding sequence inserted at the restriction site. Preferably the expression vector should include at least a portion of a bacterial plasmid. This enables the yeast expression vector to be manipulated in a bacterial host system (e.g. E. coli).

We have used two types of yeast replication origin and selective marker which are known to the art of yeast replication vector construction. The first is based on the replication region of the natural yeast plasmid 2μ (2 micron). This plasmid is cryptic, that is it confers no readily detectable phenotype and it is present in about 100 copies per cell. In a particular example a 3.25kb fragment from a 2μ plasmid derivative pJDB219 (Beggs (1978) Nature 275 104) has been used. The fragment concerned comprises two EcoRI fragments (2.5kb and 0.75kb) as follows:

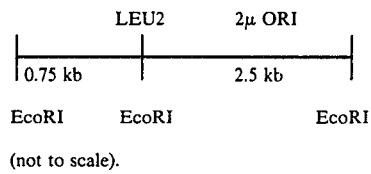

(not to scale).

The LEU2 selective marker surrounds the internal EcorRI site and may be disrupted by cleavage at this site. The 2μ sequences have been described in detail (Hartley and Donelson (1980) Nature 286 560) and the LEU2 region has also been the subject of study (Dobson et al (1981) Gene 16 133). The 3.25kb EcoRI fragment shown above has been used in the expression vectors of the present invention as a selection/replication module. Expression vectors of the present invention including the fragment may be stably maintained in yeast with a copy number of about 50–100 plasmids per cell.

The second type of yeast replication origin and marker sequence depends upon autonomous replicating sequences (ARS) derived from yeast chromosomal DNA. The best characterised of these sequences is 1.45kbp EcoRI fragment which contains both the yeast TRP1 gene and an ARS (ARS1) (Kingsman et al (1979) Gene 7 141 and Struhl et al (1979) P.N.A.S. 76 1035). This fragment has been inserted into pBR322 (a bacterial vector) to give the plasmid known as YRp7, which is capable of replication in both E. coli and yeast host systems. The ARS-based plasmids are extremely unstable, being lost almost entirely in the absence of selection and being maintained at only about 50% in the presence of selection, unless a second sequence, an ARS stabilising sequence (or ASS) is covalently joined to the ARS sequence. It now seems likely that an ASS is a centromeric DNA sequence (L. Clarke and J. Carbon (1980) Nature 287 504). A useful fragment is the 1.45kb TRP1: ARS EcoRI fragment modified to contain a 627 Sau3a fragment which contains an ASS:

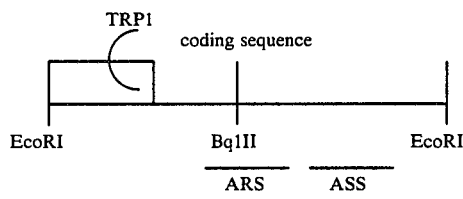

(not to scale).

The EcoRI fragment shown immediately above has been used in the expression vectors of the present invention as a selection/replication module. Expression vectors of the present invention containing this fragment may be stably maintained in yeast with a copy number of about 1 plasmid per cell. They segregate in an ordered fashion at mitosis and meiosis.

According to the present invention there is further provided a yeast expression vector wherein the yeast promoter comprises at least a portion of the 5' region of a gene coding for a yeast glycolytic enzyme. The yeast glycolytic enzyme may be; phosphoglucose isomerase, phosphofructo kinase, aldolase, triose phosphate isomerase, glyceraldehyde 3 phosphate dehydrogenase, enolase pyruvate kinase, phosphoglycerate kinase.

Especially preferred is a yeast expression vector wherein the yeast promoter comprises at least a portion of the 5' region of the yeast phosphoglycerate kinase (PGK) gene. Yeast expression vectors which include at least a portion of the 5' region of a yeast glycolytic enzyme are susceptible to expression control by varying the level of a fermentable carbon source in the nutrient medium of a yeast transformed with such a vector. A preferred fermentable carbon source is glucose. In a further preferred aspect of the present invention we provide a yeast expression vector wherein at least a portion of the 5' region of the PGK gene is located upstream of the unique restriction site and at least a portion of the 3' region of the PGK gene is located downstream of the unique restriction site. The terms "upstream" and "downstream" relate to the direction of transcription and translation.

In an alternative aspect of the invention we provide a yeast expression vector wherein the yeast promoter comprises at least a portion of the 5' region of the TRP1 gene.

The expression vectors of the present invention include a yeast replication origin and a yeast selective marker. In a preferred embodiment these may comprise a fragment containing at least a portion of the yeast plasmid 2μ replication origin and at least a portion of the LEU2 yeast selective marker. In an alternative preferred embodiment these may comprise a fragment containing at least a portion of an autonomous replicating sequence and at least a portion of an autonomous replicating sequence stabilising sequence.

A gene inserted into a yeast expression vector of the present invention may be expressed as a fusion protein in the correct reading frame depending upon the vector chosen.

In a preferred embodiment of the present invention we provide a yeast expression vector containing at least a portion of a gene coding for a polypeptide, preferably human interferon-α.

According to another aspect of the present invention we provide a process for the production of a polypeptide comprising expressing the said polypeptide in a yeast host organism transformed by a yeast expression vector containing a gene coding for the said polypeptide.

According to another aspect of the invention we provide a kit of yeast expression vectors. The kit may comprise two or more yeast expression vectors of the present invention. The object of providing such a kit is to facilitate the molecular biologist's routine expression work by affording him a variety of vectors having either high or low copy number per cell and either high or low levels of expression. The reading frame of inserted DNA may also be selectable by choice of an appropriate vector from the kit. In a preferred embodiment we provide a kit comprising four or more yeast expression vectors wherein each vector has either of the TRP1:ARS1:ASS or LEU2:2μ replication origin selective marker and replication systems and at least a portion of either of the TRP1 or PGK 5' region yeast promoters.

The present invention is now described with reference to the following Examples and to the accompanying drawings in which:

FIG. 6 is a nucleotide sequence showing the sequence of the TRP1 5' control region;

Figure 9:
FIG. 9(a) is an amino sequence showing the sequence of residues 270–400 of yeast PGK.
FIG. 9(b) is a partial endonuclease map of the 1.95kb Hind III fragment.
Figure 10:
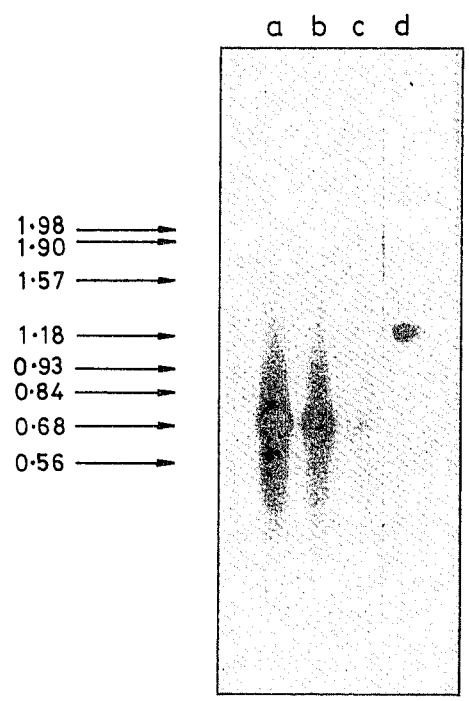
Figure 11:
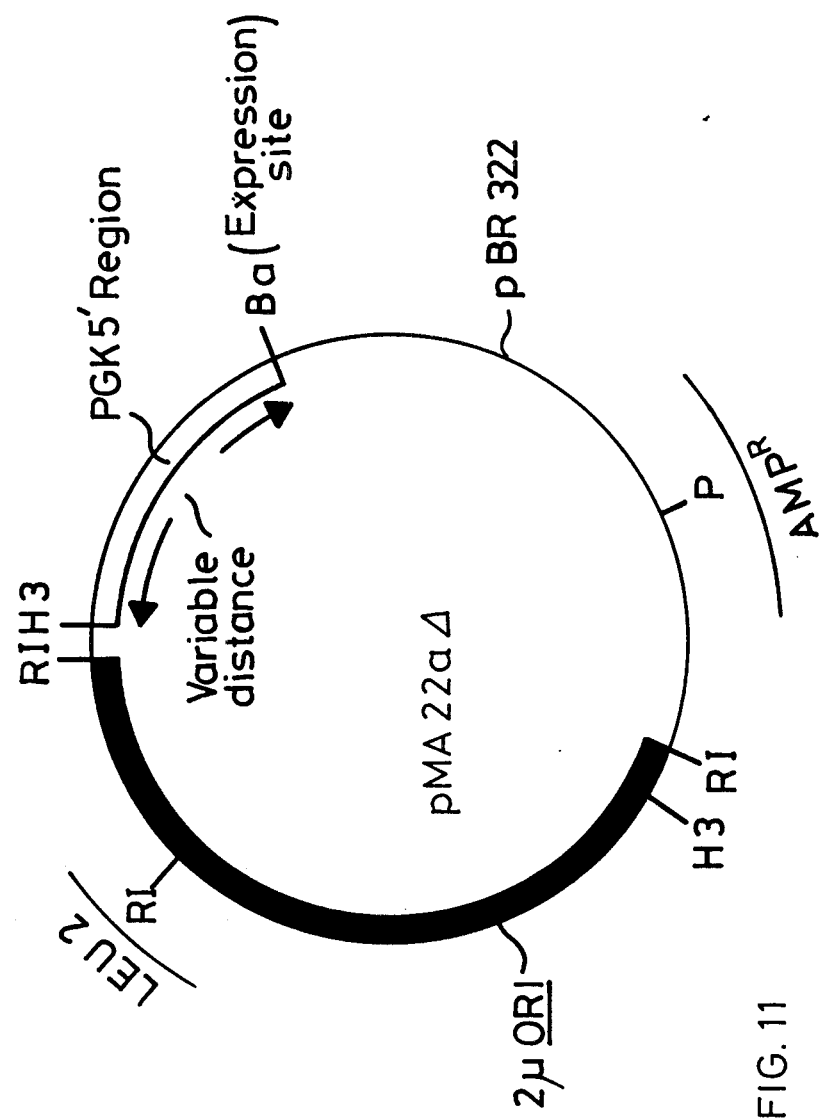
Figure 15:
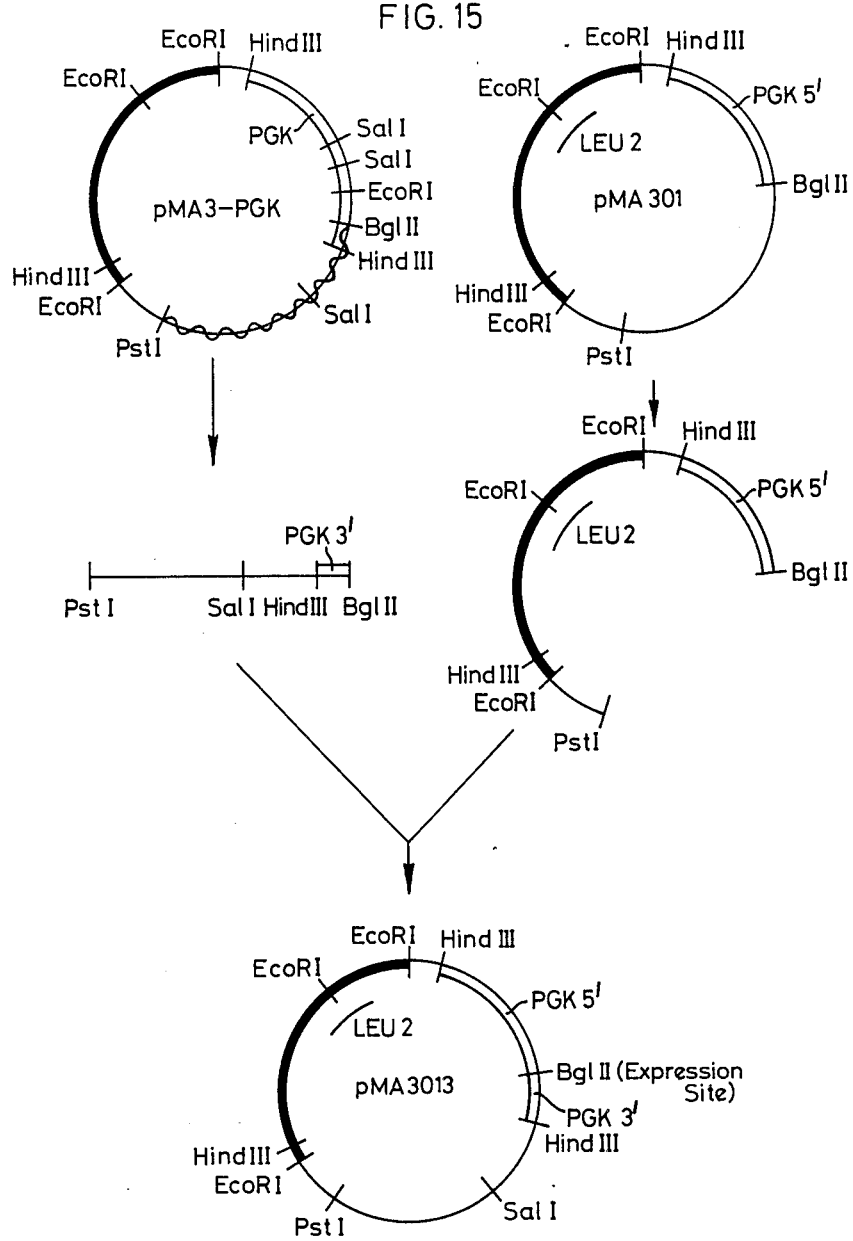
Figure 17:
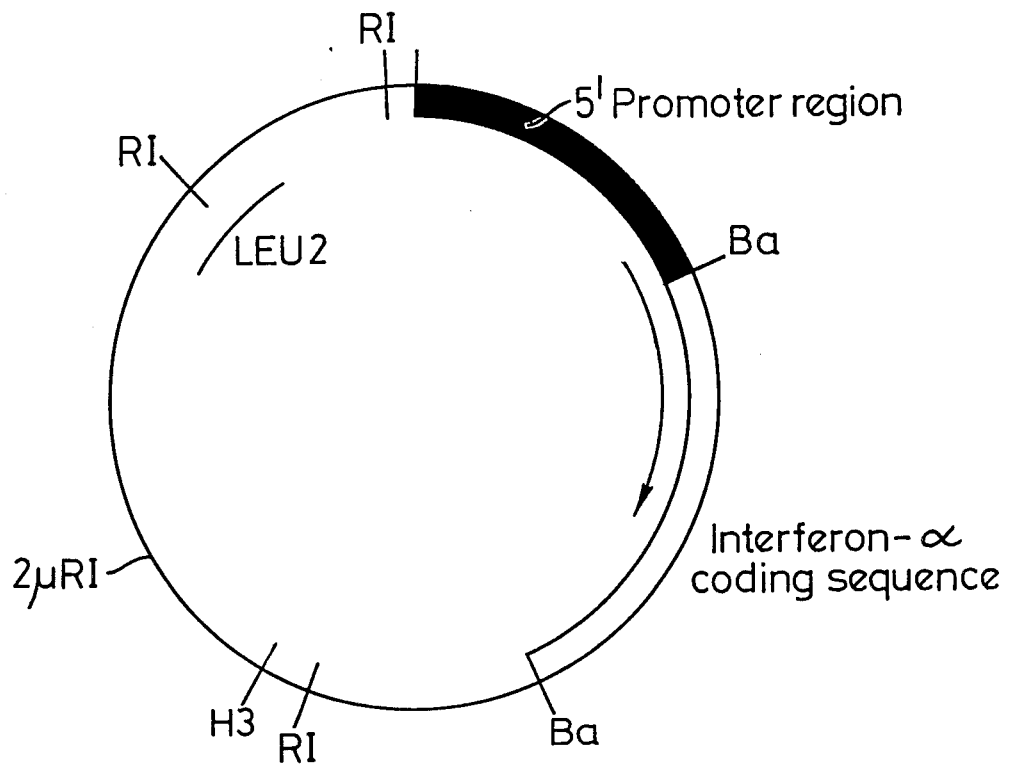
Figure 18:
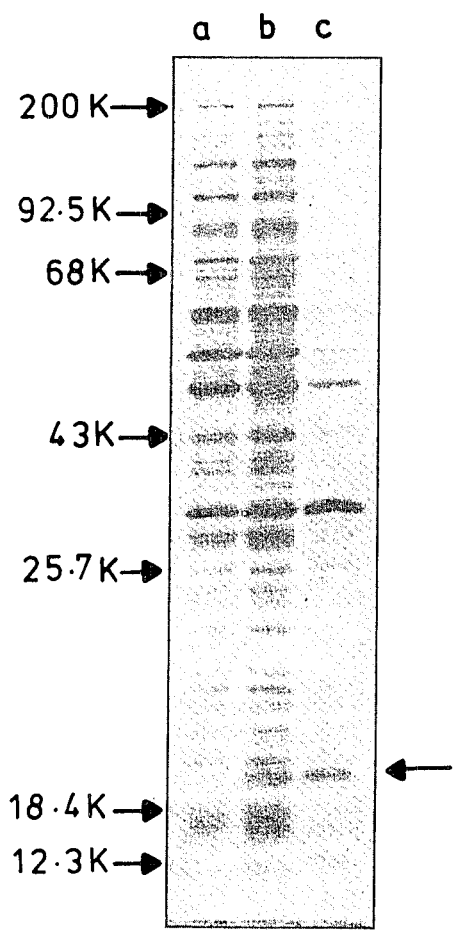
Figure 19:
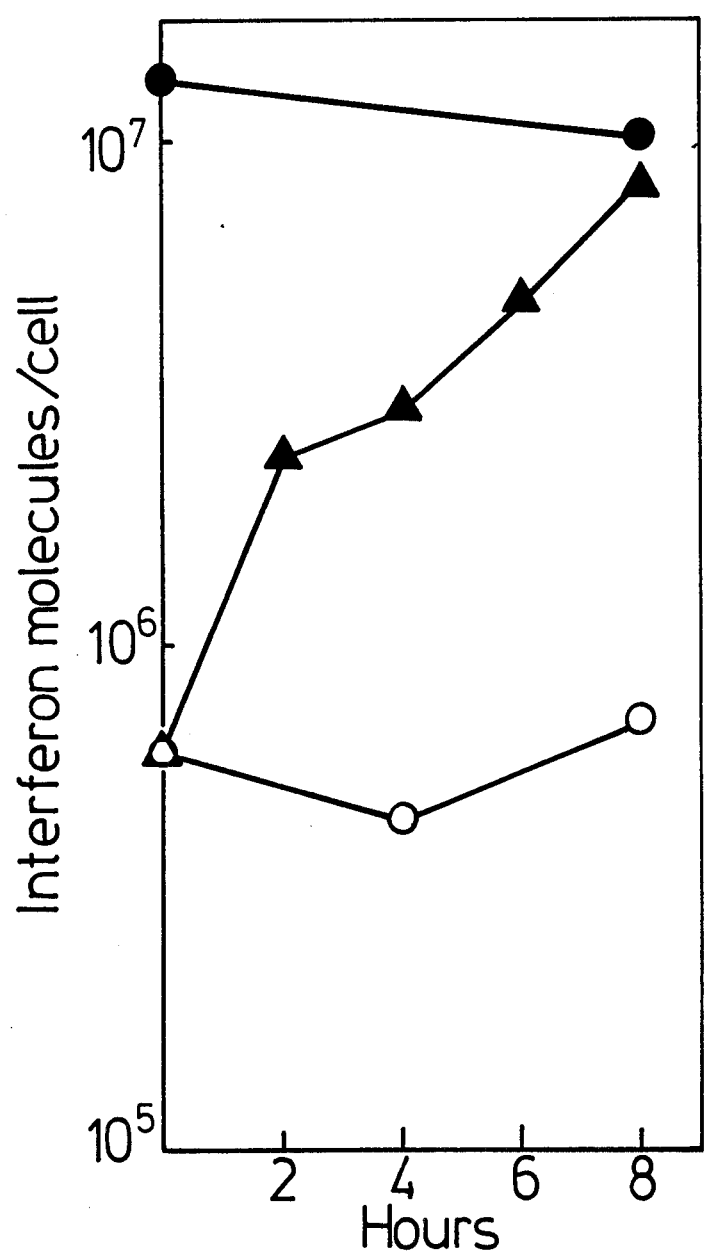

(FIGS. 9(a) and 9(b) allow a comparison of the PGK amino acid sequence and restriction sites);

FIG. 10 shows the results of a SI RNA protection of the Hae III fragment spanning the 5' end of the PGK coding sequence;

FIG. 11 is a partial restriction endonuclease map showing the general structure of the pMA22a deletion series;

FIG. 12 is a nucleotide sequence showing the sequence of the 5' region of the PGK gene;

FIG. 13 is a nucleotide sequence showing the sequence of the PGK gene from −226 to +624 with various deletion end points marked;

FIG. 14 is a nucleotide sequence showing the sequence at the 3' end of the PGK from EcoRI site to nucleotide 140 beyond the stop codon;

FIG. 15 is a schematic diagram showing the construction of yeast expression plasmid pMA3013;

FIG. 16 is a nucleotide sequence showing the sequence of a modified BamHI human interferon-α gene fragment;

FIG. 17 is a partial restriction endonuclease map showing a generalised interferon yeast expression plasmid;

FIG. 18 is a reproduction of a Coomassie stained SDS-PAGE gel showing (marked with an arrow) the production of a interferon fusion protein, produced by pMA230;

FIG. 19 is a graph showing the glucose regulation of interferon expression.

In the drawings restriction endonuclease maps are not drawn to scale. The restriction sites are in some cases abbreviated as follows:
RI=EcoRI
Pst or P=PstI
Bam or
Ba=Bam HI
Bg=Bgl II
Pv=Pvu II
Sal or S=Sal I
Ha 3=Hae III
H3=Hind III The yeast expression vectors to be described are based on the bacterial plasmid pBR322 and use one or other of the yeast replication origin/selective marker modules described above. Both modules are EcoRI fragments and are therefore readily manipulated.

We have constructed, using standard techniques, a vector designated pMA3 which is composed of the *E. coli* vector pBR322 and the EcoRI fragment containing part of the 2μ yeast plasmid as described above. This plasmid in contrast to many known chimaeric yeast plasmids appears to be relatively stable and is maintained in yeast at a high copy number of about 50–100 plasmids per cell.

We have constructed, again using standard techniques, a second vector designated pMA91 which is composed of the *E. coli* vector pBR322 and the ARS:ASS EcoRI fragment described above. This plasmid is again stable in yeast but is present at a copy number of 1.

Figure 1:
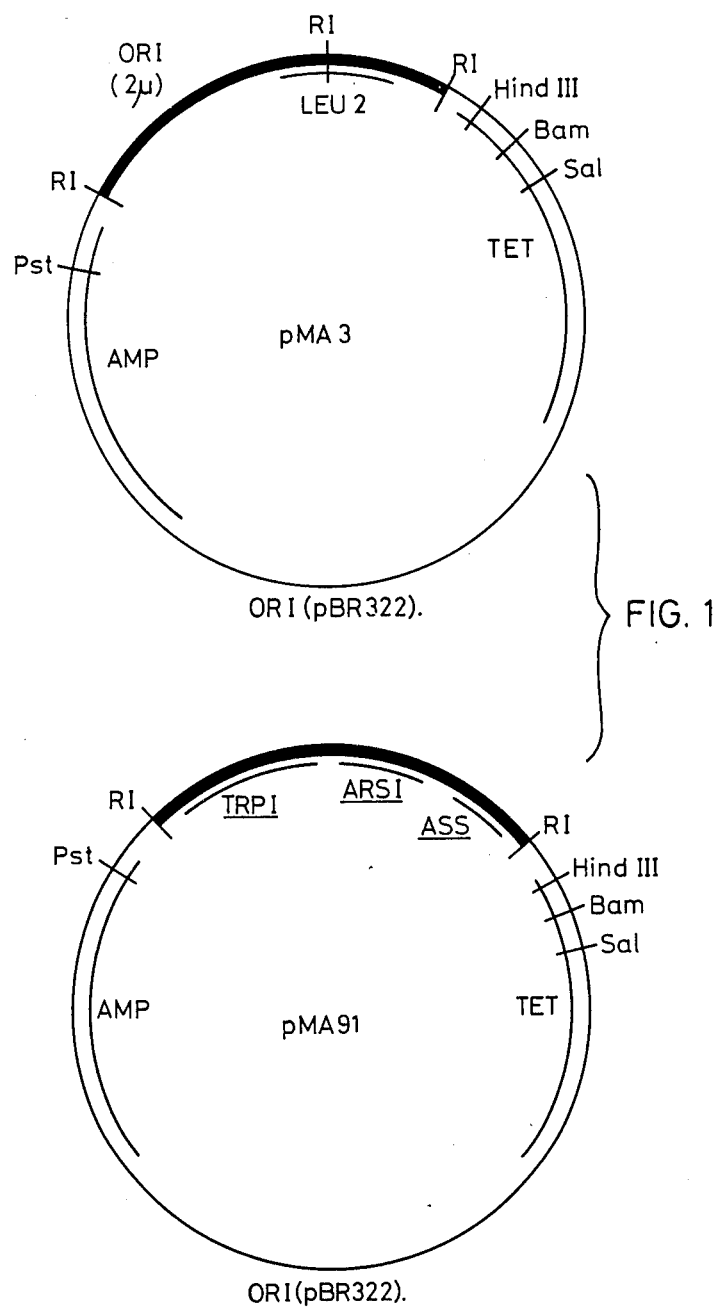
FIG. 1 is a partial restriction endonuclease map of two yeast replication vectors used as precursors in the construction of expression vectors of the present invention. They are designated pMA3 and pMA91.

The two vectors pMA3 and pMA91 are described by partial maps in FIG. 1. They are not vectors falling within the ambit of the present invention but rather important precursors in the production of vectors of this invention. In each case in FIG. 1 the thick line indicates the sequence derived from yeast DNA.

pMA3 and pMA91 DNAs were prepared by standard procedures (Chinault and Carbon (1979) Gene 5 111). pMA3 was partially digested with EcoRI and the products separated on a 1% agarose gel. The 3.25kb double EcoRI fragment containing the 2μ origin of replication and the LEU2 gene was purified by the method of Tabak and Flavell (1978) Nucleic Acids Res. 5 2321). Similarly pMA91 was digested to completion with EcoRI and the 1.0kb fragment containing the TRP1 gene, ARS1 and an ASS was purified. Two DNA fragments were therefore available as replication/selection system modules. These are referred to hereinafter as the 2μ:LEU2 module and the TRP1:ARS1:ASS module respectively.

In the specific embodiment of the invention to be described in the expression vectors contain one of two types of useful functional promoter sequence. The first comes from the 5' region of the yeast TRP1 gene and the second from the 5' region of the yeast PGK gene. In some of the vectors the 3' region of the yeast PGK gene has been included.

Figure 2:
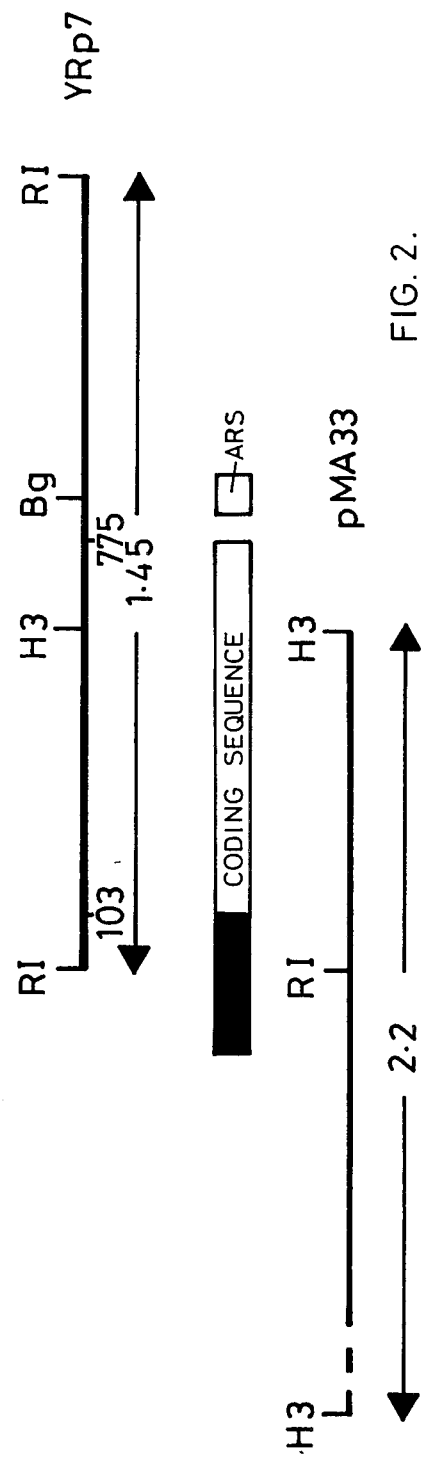
FIG. 2 is a partial restriction endonuclease map of overlapping EcoRI fragments of the TRP1 gene.

The 1.45kb EcoRI fragment containing the yeast TRP1 gene and the ARS1 has been completely sequenced (Tschumper and Carbon (1980) Gene 10 157). The organisation of the fragment is shown in FIG. 2 in which the shaded area to the left of the TRP1 coding sequence is the 5' region of the gene. The 5' control region has considerable homology with the analogous regions of the iso-1-cytochrome C and GPD genes from yeast (Smith et al (1979) Cell 16 759) Holland & Holland (1979) JBC 254 5466). In each case there is a region containing a purine rich strand of about 30 nucleotides which terminates 48–76 nucleotides up-stream from the initiation codon. There is also a CACACA sequence 10–15 nucleotides up-stream from the initiation codon. This hexanucleotide has been seen only in yeast and its proximity to the initiation codon may implicate it in translation, possibly ribosome binding, although the existence of ribosome binding sites other than the 5' CAP-structure in eukaryotes seems in doubt (Naksishima et al (1980) Nature 156 226; Stiles et al (1981) Cell 25 277). That signals necessary for TRP1 expression are within the 5' flanking region on the 1.45kb fragment in plasmid YRp7 (FIG. 2) is certain since the gene is expressed with the fragment in both orientations in pBR322. However, it is likely that all the signals for maximal TRP1 expression are not present since there are only 103 nucleotides 5' to the initiating ATG and most eukaryotic genes possess 5' control regions considerably longer than this. A 95bp EcoRI-AluI fragment at the very left end of the 1.45kb EcoRI fragment (as shown in FIG. 2) should contain signals sufficient for TRP1 expression since the AluI site is only 8 nucleotides away from the initiating ATG. This fragment therefore provides a potentially useful "mobile promoter" although additional sequences up-stream from this fragment may be necessary for maximal expression. The level of expression from the promoter is expected to be relatively low since TRP1 mRNA is present in about 0.1–0.01% of total mRNA.

The second available yeast promoter sequence is that of the phosphoglycerate kinase (PGK) gene isolated originally by Hitzeman et al (1979), ICN-UCLA SYMP. 14 57). The cloned PGK gene is less well characterised than TRP1 but is potentially more useful for higher levels of expression in yeast as the single structural PGK gene produces 1–5% of total polyA-mRNA and protein. The glycolytic enzyme genes of yeast are regulated by carbon source (Maitra and Lobo (1981) JBC 246 475) giving the potential of developing a simple control system for the production of heterologous proteins in yeast. Analysis of protein and nucleic acid sequences have enabled us to define the co-ordinates of the PGK coding sequence.

In summary two plasmids, high and low copy number, and two promoter sequences, high and low expression, are available for use in yeast expression system. It is one aim of the invention to provide a set of vectors suitable for the expression, at various levels, of "useful" genes in yeast so that expression characteristics for a given heterologous protein can be determined quite simply by selecting the appropriate plasmid.

This set comprises all four pairwise combinations of the two promoters, TRP1 and PGK and the TRP1:ARS1:ASS and LEU2:2μ replication origin, selective marker and replication systems. In addition the kit contains molecules based on the PGK expression system which will permit fusion of useful polypeptides to the amino-terminal amino acids of yeast phosphoglycerate kinase in all three codon reading frames. In PGK based expression systems expression can be regulated by the availability of glucose. The kit will, therefore, cover all possible expression, selection and replication requirements so that any polypeptide coding sequence, complete or partial, can be expressed under almost any control condition. Table 1 lists the designations of the plasmids in the kit and lists their basic properties.

TABLE 1

| | *Saccharomyces Cerevisiae* Expression Kit | | |
|---|---|---|---|
| Plasmid class/number | E. coli Selection & Replication System | Yeast Selection & Replication | Expression System |
| pMA 103 | Ampicillin$^R$ PBR322 | LEU2:2μ | TRP1 |
| pMA 113 | Ampicillin$^R$ PBR322 | TRP1:ARS1:ASS | TRP1 |
| pMA 36 | Ampicillin$^R$ PBR322 | LEU2:2μ | TRP1 (extended) |
| pMA 200 p | Ampicillin$^R$ PBR322 | " | PGK |
| pMA 200 f1 | Ampicillin$^R$ PBR322 | " | PGK |

TABLE 1-continued

Saccharomyces Cerevisiae Expression Kit

| Plasmid class/number | E. coli Selection & Replication System | Yeast Selection & Replication | Expression System |
|---|---|---|---|
| pMA 200 f2 | Ampicillin$^R$ PBR322 | " | PGK |
| pMA 200 f3 | Ampicillin$^R$ PBR322 | " | PGK |
| pMA 250 p | Ampicillin$^R$ PBR322 | TRP1:ARS1:ASS | PGK |
| pMA 250 f1 | Ampicillin$^R$ PBR322 | " | PGK |
| pMA 250 f2 | Ampicillin$^R$ PBR322 | " | PGK |
| pMA 250 f3 | Ampicillin$^R$ PBR322 | " | PGK | p = vector expresses by transcription promotion
f1 = vector produces fusion protein with junction between codons
f2 = vector produces fusion protein with junction at PGK reading frame +1
f3 = vector produces fusion protein with junction at PGK reading frame +2

EXAMPLE 1

Figure 3B:
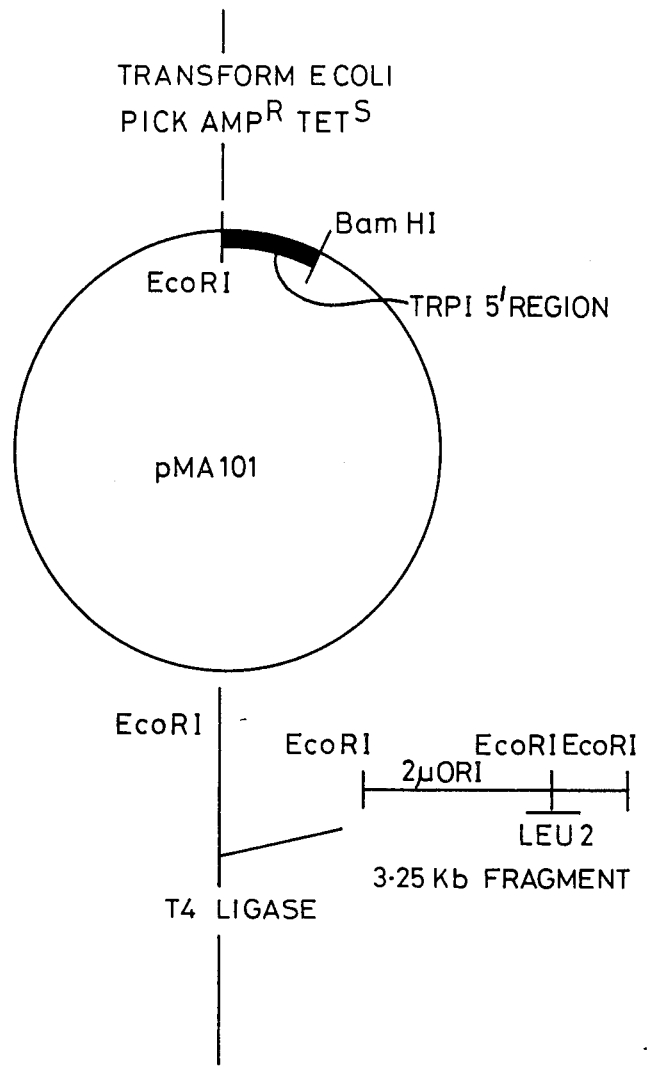
FIG. 3 is a schematic diagram showing the construction of yeast expression vector pMA103.
Figure 4:
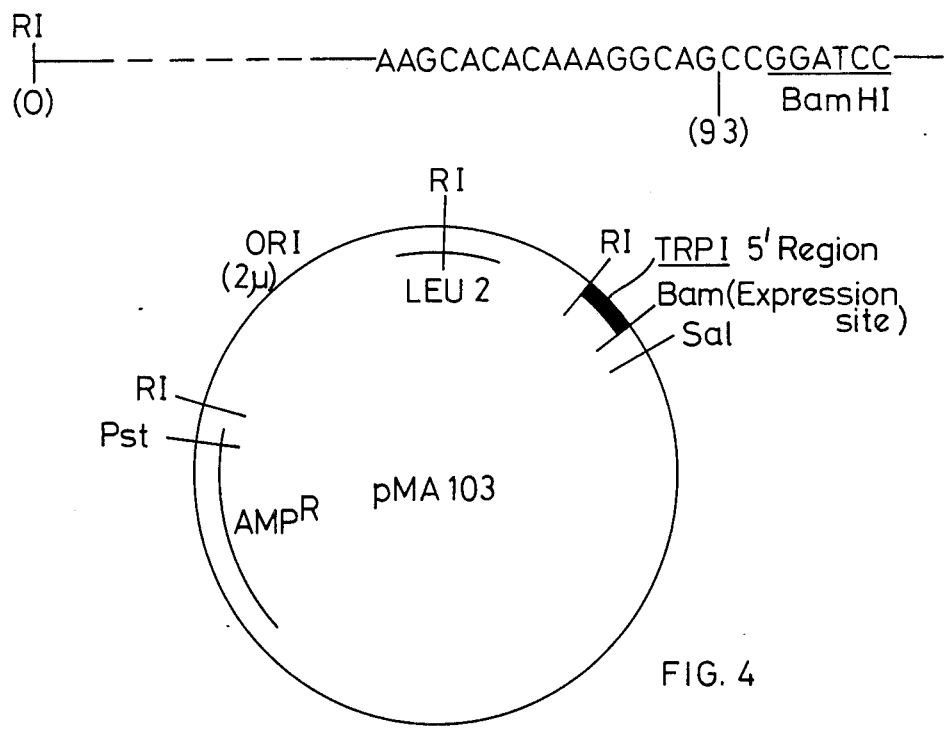
FIG. 4 is a partial restriction endonuclease map of yeast expression vector pMA103.

A number of yeast expression vectors based on the 5' region of the yeast TRP1 gene were constructed. The scheme for the construction of yeast expression plasmid designated pMA103 is shown in FIGS. 3(a), 3(b). Partial restriction endonuclease site maps and sequence information are shown; detailed information is in Tschumper and Carbon (1980) Gene 10 157 Hartley and Donelson (1980) Nature 286 860 and Sutcliffe (1979) C.S.H.S.Q.B.43 79). The use of T4 ligase and Bam HI linkers is according to Maniatis et al (1978) Cell 15 687 and restriction fragment purification from polyacrylamide gels was by the method of Maxam and Gilbert (1980) Methods in Enz. 65 499. E. coli transformation was as described in Cameron et al P.N.A.S. (1975) 72 3416. The AluI site which defines one terminus of the EcoRI-AluI fragment at the 5' end of the TRP1 gene is located only 8 nucleotides up-stream from the ATG initiation codon. Therefore any sequence inserted at this AluI site should be efficiently transcribed from the TRP1 promoter. If the sequence also contains an ATG initiation codon close to the 5' end we would also expect efficient translation. Therefore the EcoRI-AluI fragment (93bp) was purified from other restriction fragments produced by an EcoRI and AluI digest of YRp7 after fractionation on a 7% acrylamide gel. This fragment was then ligated to pBR322 cleaved with EcoRI and BamHI linkers, more ligase and spermidine was then added to the reaction. After incubation for 6 h at 20° C. the DNA was phenol extracted ethanol precipitated and then digested with BamHI to cleave the linker. The BamHI was then removed by phenol extraction and the mixture of molecules ligated and used to transform E. coli AKEC28. (AKEC 28=K.12 trpC1117 leuB6 Thy hsdr$^-$hsdm$^-$). Transformant colonies containing plasmid which had the small EcoRI-BamHI fragment of pBR322 replaced by the 93bp EcoRI-AluI fragment from YRp7 with a BamHI linker attached to the AluI terminus were identified on the basis of their tetracycline sensitivity, their positive signal in a "Grunstein and Hogness" hybridisation ((1975) P.N.A.S. 72 3961) with the 1.45kb TRP1:ARS1 fragment as probe and subsequently by a detailed restriction analysis of their plasmid DNA. The plasmid thus formed is pMA101 FIG. 3b). pMA101 was then cleaved at its unique EcoRI site, mixed with the 2μ:LEU2 replication/selection module, ligated and used to transform E. coli AKEC 28 selecting for ampicillin resistance and leucine prototrophy. All transformants of this phenotype contained molecules with the same map as that shown as pMA103 FIG. 4 or with the 2μ:LEU2 module in the other orientation. The expression site in pMA103 is BamHI and it transforms yeast at a frequency of $10^5/\mu g$.

Figure 5:
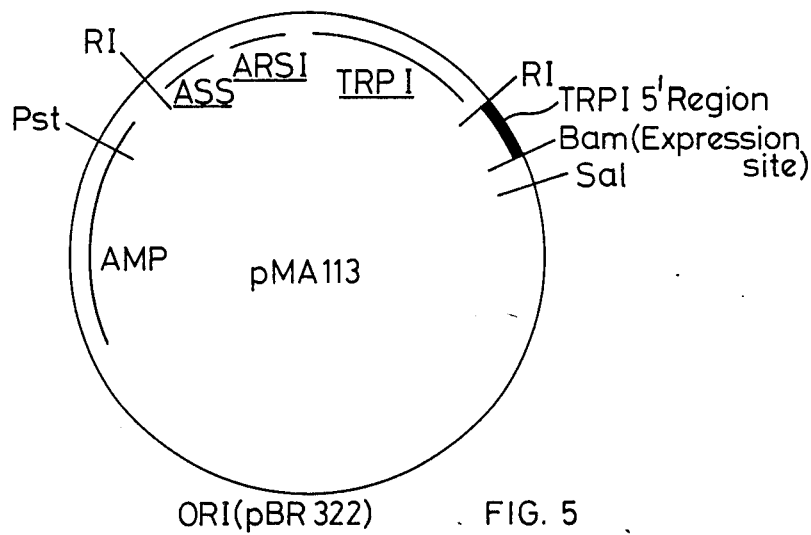
FIG. 5 is a partial restriction endonuclease map of yeast expression vector pMA113.

Similarly the TRP1:ARS1:ASS module was inserted into the EcoRI site of pMA101 to construct pMA113 but in this case selection was for ampicillin resistance and tryptophan prototrophy. A partial map of pMA113 is shown in FIG. 5. The yeast transformation frequency is $10^4/\mu g$ with pMA113.

EXAMPLE 2

A region of the yeast genome beyond the bounds of the 1.45kb EcoRI TRP1 fragment was cloned in order to make use of the entire TRP1 5' control region.

Figure 7:
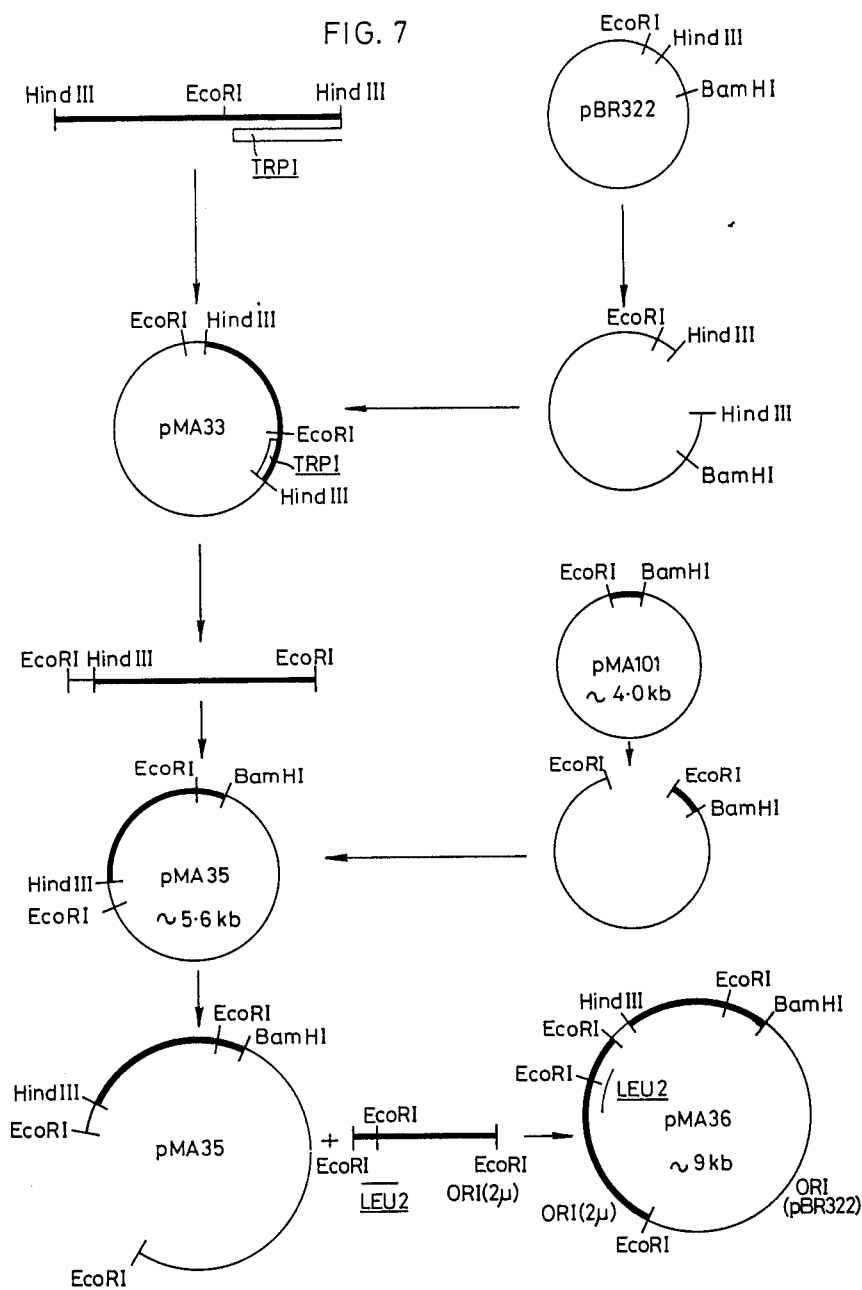
FIG. 7 is a schematic diagram showing the construction of yeast expression plasmid pMA36.

DNA sequences beyond the limits of the 1.45kb EcoRI:TRP1 fragment are required for maximal expression from the TRP1 promoter. We isolated the Hind III fragment that overlaps the 1.45kb EcoRI fragment and which contains the entire TRP1 5' control region (shown as the shaded area FIG. 2). In order to find the size of that Hind III fragment we used the smaller of the EcoRI-Hind III fragments from the 1.45kb EcoRI fragment (FIG. 2) as a probe in a Southern hybridisation to total yeast DNA cleaved with Hind III. A single, approximately 2.0kb band was visible after autoradiography. Hind III digested total yeast DNA was then distributed in a 1% agarose gel and all the DNA in the size range 1.5-2.5kb was purified by the method of Tabak & Flavell (1978) NAR 5 2321) and ligated with Hind III digested pTR262 (Roberts et al (1980) Gene 12 123). 700 Tetracycline resistant colonies were then screened by the "Grunstein-Hogness" procedure using the purified 1.45kb EcoRI:TRP1 fragment as a probe. A single colony showed hybridisation with this probe and plasmid DNA was prepared from this clone. The plasmid contained a 2.2kb Hind III fragment which hydridised specifically to the smaller of the EcoRI-Hind III fragments from the 1.45kb EcoRI TRP1 fragment. The nucleotide sequence of the region up-stream from the EcoRI site at position-103 (A in ATG is +1) was determined by standard M13/dideoxy sequencing procedures (Sanger et al (1977) P.N.A.S. 74 6463) and is shown in FIG. 6. In this Figure the nucleotide sequence from 169 to 275 was after Ischumper and Carbon (1980) Gene 10 157. Potentially important features are underlined. New sequence data includes all sequences not overlined. In order to construct a derivative of pMA103 that contains the entire TRP1 5' control region a set of constructions were performed as outlined in FIG. 7. (In this Figure the thick lines indicate DNA derived from yeast). The 2.2kb Hind III fragment was purified by the method of Tabak & Flavell (1978) NAR 5 2321) and inserted into the Hind III site of pBR322 to form plasmid pMA33. The small EcoRI fragment from pMA33 was purified and then inserted into the unique EcoRI site of pMA101 (see FIG. 3(b)). The orientation of the fragment was checked to ensure reconstitution of the TRP1 5' region. The resulting plasmid is designated pMA35. pMA35 was then cleaved partially with EcoRI and the 2μ:LEU2 module inserted. Recombinant molecules were screened for the presence of the 2μ:LEU2 fragment at the pBR322 EcoRI site rather than the EcoRI site at −103. Such a molecule is pMA36 (FIG. 7).

EXAMPLE 3

A number of yeast expression vectors based on the 5' region of the yeast PGK gene were constructed.

The yeast PGK gene exists on a 2.95kb Hind III fragment in the yeast-*E.coli* vector, pMA3, (FIG. 1). A partial restriction map of this molecule is shown in FIG. (8a). The PGK Hind III fragment was isolated from a Hind III fragment collection inserted into λ762 (Murray et al (1977) Molec.gen.Genet 150 53) using a $^{32}$P labelled cDNA prepared from yeast poly-A RNA. The fragment is identical to the "3.1kb" fragment described in Hitzeman et al (1980) JBC. 255, 12073 in plasmid pB1 and in hybrid selection translation experiments (Ricciardi et al (1979) P.N.A.S. 76 4927) the fragment was shown to encode a protein of identical mobility to pure PGK in SDS-PAGE. A restriction map of the 1.95kb fragment is shown in FIG. 8(b).

The amino acid sequence of residues 270–400 of yeast PGK is shown in FIG. 9(a). The sequence was determined by manual and automated Edman degradation. The amino acid sequence data allowed us to match restriction sites on the 2.95kb Hind III fragment with groups of two or three amino acids in the protein sequence. FIG. 9(b) shows the relevant restriction sites and those sites are marked on the amino acid sequence in FIG. 9(a). The positions of the four sites on the restriction map and the protein sequence are congruent allowing us to orientate the gene with respect to the sites on the 1.95kb Hind III fragment. Given that the molecular weight of PGK is 40Kd (415 amino acid residues) and assuming that there are no large introns we can also predict the positions of the 5' and 3' ends of the coding sequence. The extent of the coding sequence, assuming colinearity, is shown in FIG. 8(b), the initiation codon is about 900 nucleotides to the left of the EcoRI site and the termination codon about 300 nucleotides to the right.

The position of the 5' end of the PGK transcript was located by the S1 protection method (Berk and Sharp (1978) P.N.A.S. 75 1274). The 1.2kb Hae III fragment spanning the 5' end of the coding sequence (FIG. 8(b) was purified from an agarose gel and hybridised to total yeast RNA. The hybrids were treated with various concentrations of S1 nuclease and the products were analysed on a 1.5% agarose gel by Southern hybridisation using the 1.95kb Hind III fragment as probe. FIG. 10 shows that the size of the single protected fragment was 680bp. In this Figure the concentrations of S1 in each lane are as follows (a) 25 units (b) 50 units (c) 100 units. Lane (d) has the 1.2kb Hae III fragment untreated. On the basis of our previous mapping data this would place the 5' end of the PGK transcript about 960bp to the left of the EcoRI site on the 2.95kb Hind III fragment. This agrees well with our estimate of the position of the initiation codon and suggests that if there are any introns between the 5' end of the transcript and the Bgl II site than they are very small.

Figure 8:
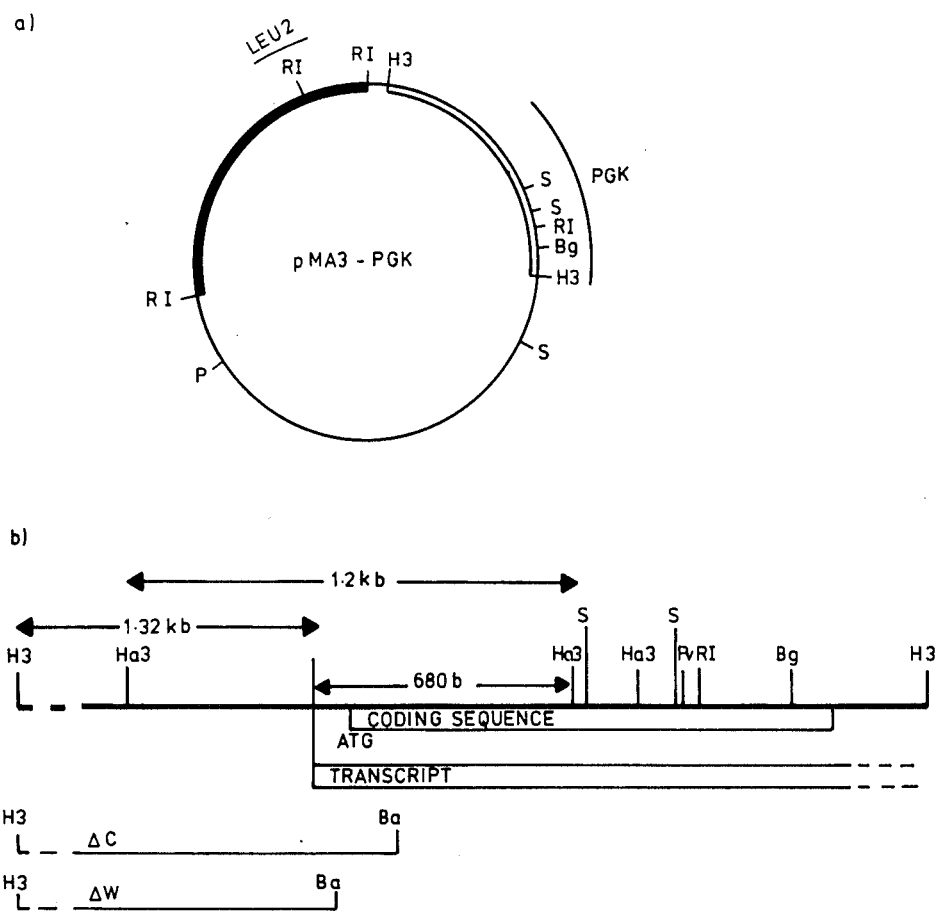
FIG. 8(a) is a partial restriction endonuclease map of the plasmid pMA3-PGK showing the location of the yeast PGK gene.
FIG. 8(b) is a map of the 2.95kb Hind III fragment of pMA3-PGK.

The 5' "control" region of the PGK gene is in a region that contains very few convenient restriction sites, making the design of a sequencing strategy relatively difficult. We adopted a procedure to solve this problem that may be of general use. Plasmid pMA3-PGK was digested with Sal I (FIG. 8) and then with exonuclease BAL 31 to remove about 500bp from each end. This resulted in the loss of the two small Sal I fragments and the creation of a series of deletions starting at the leftmost Sal I site in the PGK sequence and the Sal I site in pBR322 and ending around the initiation codon in PGK and nucleotide 1150 in pBR322 respectively. These deleted molecules were then ligated in the presence of a 50-fold molar excess of Bam HI linkers and then used to transform AKEC28 to LEU+, Amp$^R$. The general structure of these molecules, designated the pMA22a deletion series is shown in FIG. 11. Seventy of these deleted molecules have been analysed by measuring the length of the EcoRI-BAM HI fragment containing the 5' region of the PGK gene. While they show a mean length of 1.5kb they have a spread of 500 nucleotides. This collection therefore provides a number of molecules that are useful for the sequence analysis of the 5' region of the PGK gene. Two such deletions, C and W are shown in FIG. 8(b). The small EcoRI-Bam HI fragments from these molecules were purified and cloned in M13mp701 and sequenced by the dideoxy-chain termination method Sanger et al (1977) P.N.A.S. 74 5463, starting in each case at the Bam HI site and elongating towards the EcoRI site. The nucleotide sequence of 226 nucleotides up-stream from the inition codon and the first seven codons are shown in FIG. 12. (In this Figure the box marks the approximate position of the 5' end of the transcript). The sequence was confirmed by sequencing four other deletions with overlapping endpoints (data not shown).

The pMA22a deletion series constitutes a collection of molecules amongst which are many potential PGK based expression vectors. Each with a different sized small EcoRI-BAM HI fragment and therefore each with a different "amount" of the PGK 5' region. They all have unique Bam HI sites at which genes may be inserted and expressed. FIG. 13 shows the sequence of the PGK gene from −226 to +624 with the positions of various deletion end-points marked. The deletion end point numbers (FIG. 13) are carried through to the name of the plasmid that bears that deletion e.g. plasmid pMA279 is a pMA22a deletion with the deletion endpoints between the codons for amino acids 32 and 33. At that position the Bam HI linker of sequence CCGGATCCGG has been inserted. At each of the deletion end-points there is the same BAM HI linker with the exception of pMA301 which has the Bgl II linker CAAAAGATCTTTTG inserted at position −1. This Bgl II linker was used in order to increase the A content of the region around the initiating ATG.

Clearly plasmids pMA278 and pMA301 will produce transcriptional fusions with any coding sequence inserted at their expression sites and are therefore of the pMA200p type in Table 1, whereas all the others will produce both transcriptional and translational fusions (i.e. fusion proteins will be made). pMA230 is a +1 (reading frame) fusion vector, pMA283 is an in frame (+3) fusion vector. The molecules are of the pMA200f1, f2 and f3 type in Table 1.

EXAMPLE 4

We have constructed a PGK based expression vector designated pMA3013 which comprises both 5' and 3' regions from the yeast PGK gene.

We have determined the nucleotide sequence of the 3' region of PGK by standard procedures and this is shown in FIG. 14. FIG. 15 shows the scheme for constructing pMA3013. Plasmid pMA3-PGK was cut with Bgl II and Pst I and the fragment containing the 3' end of the PGK gene (shown as a wavy line in FIG. 15) was purified by the method of Tabak and Flavell (1978) NAR 5 2321). This fragment was then ligated with Bgl II and Pst I cleaved pMA301 and the mix was used to transform E.coli strain AKEC28 to ampicillin resistance and leucine prototropy. Resulting clones were screened for a plasmid with three Hind III sites. Such a plasmid is pMA3013. pMA3013 has a unique Bgl II expression site flanked by the PGK 5' and 3' regions.

EXAMPLE 5

The various yeast expression vectors described have been tested using a human interferon-α as a heterologous, potentially useful coding sequence. The sequence is contained on a Bam HI fragment that is a derivative of plasmid N5H8 originally constructed by Prof. D. C. Burke, University of Warwick. Our modification places a Bam HI site followed by an ATG at a position corresponding to amino acid S15 in the interferon signal sequence. The nucleotide sequence of this Bam HI fragment is given in FIG. 16. The Bam HI fragment can be used in transcription fusion constructions because it has its own translation initiation codon and it can also be used in vectors designated to produce fusion proteins. This fragment was inserted into the expression sites of a variety of molecules the general structure of which is shown in FIG. 17. The resulting molecules were then introducted into yeast strain MD40-4C (MD40-4C=αura2 trp1leu2-3 leu2-112 his3-11 his3-15) by standard transformation procedures (Hinnen et al (1978) P.N.A.S. 75 1919) and the levels of interferon produced in yeast were measured using bovine EBTr) cells in a viral RNA reduction assay with Semliki Forest virus (SFV) as the challenge (Atherton & Burke, (1975) J. Gen.Virol 29 197). Table 2 shows levels of interferon produced in yeast cells containing various recombinant molecules.

TABLE 2
Interferon Expression from Various Vectors

| Expression Vector | 5' Region | 3' Region | Molecules of a Interferon per cell* |
|---|---|---|---|
| pMA 103 | TRP1 | — | 600 |
| pMA 36 | TRP1 (extended) | — | $1.7 \times 10^4$ |
| pMA 278 | PGK (Δ278) | — | $2.0 \times 10^4$ |
| pMA 301 | PGK (Δ301) | — | $1.5 \times 10^7$ |
| pMA 3013 | PGK (Δ301) | PGK | $1.0 \times 10^7$ |
| pMA 230 | PGK (Δ230) | — | $1.5 \times 10^7$ |
| pMA 3 (control) | — | — | <50 (not detectable) |

*These figures assume $2 \times 10^8$ units of interferon/mg.

It can be seen that there is a considerable range of expression capabilities in the system depending on which expression vector is used. The highest levels are obtained with the fusion protein vector pMA230 and the transcription vectors pMA301 and pMA3013 in which as much as 2% of the total cell protein is present as interferon protein (FIG. 18). This Figure shows Coomassie stained SDS-PAGE protein profiles in which the lanes contain
  (a) Total protein from MD40-4c containing pMA230
  (b) Total protein from MD40-4c containing pMA230/interferon
  (c) Protein from MD40-4c containing pMA230/interferon after partial purification on an NK2 column. The position of molecular weight markers are shown. An arrow marks the position of the PGK-interferon fusion protein.

All interferon producing plasmids are maintained stably for at least 40 generations as measured by the proportion of cells in the population with the phenotype conferred by the expressing plasmid.

EXAMPLE 6

PGK in yeast is "induced" by glucose, therefore it was of interest to determine whether the structures necessary for the recognition of this regulatory system are present on the 1500 nucleotide PGK fragment in for example pMA230 and if so whether human interferon-α expression could be regulated by glucose.

Yeast strain MD40-4c containing pMA230 with the interferon-α sequence inserted at the Bam HI site was grown in rich medium with acetate as carbon source for twelve generations to a density of $2 \times 10^6$ cells/ml. These cells were used as inocula for two flasks of fresh medium. One containing glucose as carbon source and the other acetate. A second batch of cells grown on glucose was used to inoculate a fresh glucose culture. Therefore there were three inoculum/culture conditions: acetate/acetate; acetate/glucose; glucose/glucose. Aliquots of these cultures were taken at various intervals, extracts were prepared and interferon levels were assayed. The results of these assays are given in FIG. 19 in which ● =glucose/glucose; ○ =acetate/acetate and Δ=acetate/glucose. The data in FIG. 19 show that the glucose/glucose culture contains relatively high interferon levels while the acetate/acetate culture has low levels over the course of the experiment. The acetate/glucose culture exhibits increasing levels of interferon after the cells are transferred to glucose medium (time 0, FIG. 19). This induction of interferon occurs over a period of about 8 hrs. and the levels of interferon produced by cells grown on glucose are 20–30 fold higher than in cells grown on acetate.

While these results strongly suggest that carbon source control of interferon levels is being mediated by the 5' control region of the PGK gene it is important to establish that there is no difference in plasmid stability in cells grown on acetate or glucose. Therefore total DNA was prepared from aliquots of yeast cells taken at various points during the experiment described in FIG. 19. The DNA was digested with EcoRI and fragments were separated on a 1% agarose gel. The fractionated bands were then blotted onto nitrocellulose and hybridised with $^{32}$P-YRp7. The pBR322 component of this probe served to measure levels of plasmid in the yeast DNA preparations while the sequence of the 1.45kb fragment were used to establish a control for amounts of DNA, transfer efficiencies and hybridisation efficiencies. In addition to this Southern blot analysis the proportion of Leu+ cells in the aliquots was measured by comparing colony counts on media with and without leucine. In all cases Southern hybridisation profiles were identical and >99% of cells were Leu+ (data not shown) showing that growth on acetate or glucose has no effect on plasmid copy number or stability.

We claim:
1. A yeast expression vector having a Saccharomyces cerevisiae promoter positioned relative to a non Saccharomyces cerevisiae polypeptide coding sequence in such a way that expression may be obtained of said polypeptide coding sequence
   wherein said Saccharomyces cerevisiae promoter consists essentially of at least a functionally active promoter portion of the 5' region of the PGK gene or at least a functionally active promoter portion of the 5' region of the TRP1 gene, said yeast expression vector also including a *Saccharomyces cerevisiae* selective marker and a *Saccharomyces cerevisiae* replication origin.

2. A yeast expression vector according to claim 1 wherein said at least a functionally active portion of the 5' region of the yeast PGK gene is located upstream of the polypeptide coding sequence and said at least a functionally active portion of the 3' region of the PGK gene is located downstream of the polypeptide coding sequence.

3. A yeast expression vector according to claim 1 expression control of which is exercised by varying the level of a fermentable carbon source in a nutrient medium of a yeast transformed therewith.

4. A yeast expression vector according to claim 3 wherein the fermentable carbon source is glucose.

5. A yeast expression vector according to claim 1 wherein the yeast expression vector contains at least a functionally active portion of the yeast 2µ plasmid replication origin and at least a functionally active portion of the LEU2 yeast selective marker.

6. A yeast expression vector according to claim 1 wherein the yeast expression vector contains at least a functionally active portion of an autonomous replicating sequence stabilising sequence.

7. A yeast expression vector according to claim 1 wherein the yeast expression vector contains a gene coding for human interferon-α.

8. A method for the production of a non *Saccharomyces cerevisiae* polypeptide comprising expressing a coding sequence for the said polypeptide in a *Saccharomyces cerevisiae* host organism transformed with a yeast expression vector according to claim 1 containing the said polypeptide coding sequence.

9. *Saccharomyces cerevisiae* transformed by a yeast expression vector according to claim 1.

10. A kit of expression vectors comprising four or more different yeast expression vectors wherein each vector has either of the TRP1:ARS1:ASS or LEU2:2µ replication origin selective marker and replication system and a *Saccharomyces cerevisiae* promoter consisting essentially of at least a functionally active portion of either of the TRP1 or PGK 5' region *Saccharomyces cerevisiae* promoter.

11. A kit of yeast expression vectors comprising two or more different yeast expression vectors, each yeast expression vector having a *Saccharomyces cerevisiae* promoter positioned relative to a *Saccharomyces cerevisiae* polypeptide coding sequence in such a way that expression may be obtained of said polypeptide coding sequence wherein said *Saccharomyces cerevisiae* promoter consists essentially of at least a functionally active promoter portion of the 5' region of the PGK gene or at least a functionally active promoter portion of the 5' region of the TRP1 gene, each yeast expression vector also including a *Saccharomyces cerevisiae* selective marker and a *Saccharomyces cerevisiae* replication origin.

* * * * *